US00PP24290P3

(12) United States Plant Patent
Egger

(10) Patent No.: US PP24,290 P3
(45) Date of Patent: Mar. 4, 2014

(54) ***HEUCHERA* PLANT NAMED 'GOTHAM'**

(50) Latin Name: ***Heuchera* hybrid**
Varietal Denomination: Gotham

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 146 days.

(21) Appl. No.: 13/506,792

(22) Filed: May 16, 2012

(65) Prior Publication Data

US 2013/0312146 P1 Nov. 21, 2013

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by medium small size glossy black to dark brown leaves, showy yellow green flowers that mature to having red tints, repeat blooming on short, dark flower stalks, small, multi-crowned, low mounding habit, and excellent vigor.

1 Drawing Sheet

Botanical denomination: *Heuchera* hybrid.
Variety designation: 'Gotham'.

BACKGROUND OF THE INVENTION

The present invention relates to a new and distinct cultivar of *Heuchera* and given the cultivar name of 'Gotham'. *Heuchera* is in the family Saxifragaceae. *Heuchera* 'Gotham' originated from a controlled cross between *Heuchera* K370-1, a proprietary non-commercial hybrid, as the seed parent, and *Heuchera* K352-3, a proprietary non-commercial hybrid, as, as the pollen parent.

Compared to the seed parent, *Heuchera* K370-1, the new cultivar has a better crown.

Compared to the pollen parent, *Heuchera* K352-3, the new cultivar has yellow green flowers rather than pink.

Compared to *Heuchera* 'Obsidian', U.S. Plant Pat. No. 14,836, the new cultivar has more crowns, much shorter flowering stems, showier flowers, and yellow green rather than red brown flowers.

Compared to *Heuchera* 'Blackout', U.S. Plant Pat. No. 20,613, the new cultivar has blacker leaves, larger, showier flowers, flowers that are yellow green rather than dull white, and the leaf lobes that are more rounded.

Compared to *Heuchera* 'Coco', U.S. Plant patent application Ser. No. 13/507,938, the new cultivar has thicker, glossier leaves and flowers yellow green rather than white in color.

This new *Heuchera* is uniquely distinguished by:

1. medium small size glossy black to dark brown leaves,
2. showy yellow green flowers that mature to having red tints,
3. repeat blooming on short, dark flower stalks,
4. small, multi-crowned, low mounding habit,
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a nine-month-old plant of *Heuchera* 'Gotham' growing in a one gallon pot in a cool greenhouse in early July in Canby, Oreg.

DETAILED PLANT DESCRIPTION

The following is a detailed description of the new *Heuchera* cultivar based on observations of two-year-old specimens growing in one gallon containers in a warm greenhouse in April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 2007, 5$^{th}$ edition.

Plant:

*Form.*—Basal rosette, herbaceous perennial.
*Hardiness.*—USDA Zone 4 to 9.
*Size.*—27 cm tall from top of the foliage to the soil and 45 cm wide.
*Habit.*—Mounding.
*Vigor.*—Excellent.

Leaf:

*Type.*—Simple.
*Arrangement.*—Rosette.
*Shape.*—Broadly ovate.
*Lobing/division.*—5 main shallow lobes with shallow secondary lobes.
*Venation.*—Palmate.
*Margins.*—Crenate, slightly undulate.
*Apex.*—Mucronulate.

*Base.*—Cordate, lobes sometimes overlapping.

*Blade size.*—Grows to 12 cm long and 11.5 cm wide.

*Texture.*—Supple.

*Surface texture.*—Glandular on top and bottom side.

*Petiole description.*—Grows to 18 cm long and 3 mm wide, glandular hairs, Greyed Purple 187A.

*Leaf color.*—Topside, spring to fall, closest to Black 203A with veins Greyed Purple 187A, bottom side same for all seasons Brown 200A; winter, topside closest to Greyed Green N189A strongly tinted Brown N200A.

Inflorescence:

*Size.*—Grows to 5 cm wide and 16 cm long.

*Type.*—Thyrse.

*Number of flowers per thyrse.*—About 32.

*Number of thyrse.*—About 10 in the first spring flush, reblooming summer to frost.

*Peduncle.*—Grows to 26 cm long, 4 mm wide at base, Greyed Purple N187B, glandular hairs.

*Pedicel.*—Variable in size, with glandular hairs, Greyed Purple N187A.

*Bloom period.*—May through October in Canby, Oreg.

Flower bud:

*Size.*—3.5 mm wide and 4.5 mm long.

*Description.*—Glandular puberulent, ovoid, down facing.

*Color.*—Yellow Green 145A on top half and Yellow Green 150D lightly tinted Greyed Purple 187B on the bottom half.

Flower:

*Type.*—Perfect.

*Shape.*—Campanulate.

*Size.*—7 mm long and 7 mm wide.

*Corolla description.*—5 petals, 3.5 mm long and 1.5 mm wide, lanceolate, reflexed, margins entire, tip acute, base attenuate, glandular on top and bottom, Yellow Green 145D.

*Calyx description.*—Campanulate, 5 mm long and 5 mm wide, with 5 lobes divided ⅓ to the base, each 3 mm wide and 2.5 mm long, glandular hairs outside and inside, tips obtuse, margin entire; color outside and inside Yellow Green 145C.

*Stamen description.*—5 in number, filaments 3 mm long, White NN155C, anthers 0.2 mm, Orange Red 30A, pollen Orange 28A.

*Pistil description.*—1, 2-beaked, 6 mm long and 2.5 mm wide, Yellow Green 145C overall; ovary 3 mm long and 2.5 mm wide, style 3 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

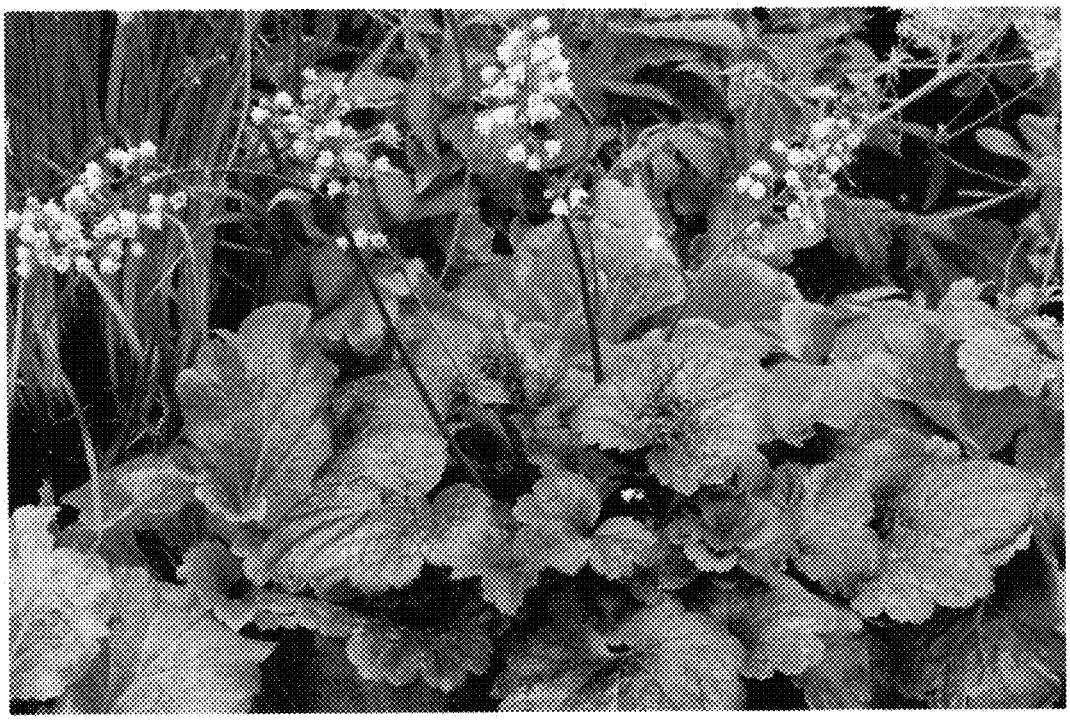

* * * * *